(12) United States Patent
Yadav et al.

(10) Patent No.: US 8,569,519 B2
(45) Date of Patent: Oct. 29, 2013

(54) PROCESS FOR THE PREPARATION OF DISPIRO 1,2,4-TRIOXOLANE ANTIMALARIALS (OZ277)

(75) Inventors: Gyan Chand Yadav, Uttar Pradesh (IN); Harish N. Dorwal, Gurgaon (IN); Srinivas Valavala, Andhra Pradesh (IN); Vinod Kumar Sharma, Punjab (IN)

(73) Assignee: Ranbaxy Laboratories Limited, New Delhi (IN)

( * ) Notice: Subject to any disclaimer, the term of this patent is extended or adjusted under 35 U.S.C. 154(b) by 741 days.

(21) Appl. No.: 12/301,823

(22) PCT Filed: May 24, 2007

(86) PCT No.: PCT/IB2007/001374
§ 371 (c)(1),
(2), (4) Date: Aug. 19, 2010

(87) PCT Pub. No.: WO2007/138435
PCT Pub. Date: Dec. 6, 2007

(65) Prior Publication Data
US 2011/0124886 A1    May 26, 2011

(30) Foreign Application Priority Data
May 24, 2006 (IN) .......................... 1252/DEL/2006

(51) Int. Cl.
*C07D 493/00* (2006.01)
(52) U.S. Cl.
USPC ..................................................... 549/340
(58) Field of Classification Search
USPC ..................................................... 549/340
See application file for complete search history.

(56) References Cited

U.S. PATENT DOCUMENTS

| 6,486,199 B1 | 11/2002 | Vennerstrom et al. | 514/462 |
| 6,906,205 B2 | 6/2005 | Vennerstrom et al. | 549/341 |
| 2004/0039008 A1 | 2/2004 | Vennerstrom et al. | 514/278 |

OTHER PUBLICATIONS

Meshnick et al., "Artemisinin and the Antimalarial Endoperoxides: from Herbal Remedy to Targeted Chemotherapy", *Microbiological Reviews*, 60(2):301-315 (1996).
Vroman et al., "Current Progress in the Chemistry, Medicinal Chemistry and Drug Design of Artemisinin Based Antimalarials", *Current Pharmaceutical Design*, 5(2):101-138 (1999).
Dhingra et al., "Current status of artemisinin and its derivatives as antimalarial drugs", *Life Sciences*, 66(4):279-300 (1999).
Jefford, 1997. Peroxidic Antimalarials. In: Meyer and Testa, eds. *Advances in Drug Research*. vol. 29. USA: Academic Press Limited, 271-325.
Dong and Vennerstrom, "Peroxidic Antimalarials", *Expert Opinion on Therapeutic Patents*, 11(11):1753-1760 (2001).
Wesche et al., "Neurotoxicity of Artemisinin Analogs In Vitro", *Antimicrobial Agents and Chemotherapy*, 38(8):1813-1819 (1994).
White, "Clinical pharmacokinetics and pharmacodynamics of artemisinin and derivatives", *Transactions of the Royal Society of Tropical Medicine and Hygiene*, 88(Suppl. 1):41-43 (1994).
van Agtmael et al., "Artemisinin drugs in the treatment of malaria: from medicinal herb to registered medication" *Trends in Pharmacological Sciences*, 20(5):199-205 (1999).
Cumming, Ploypradith, and Posner, 1997. Antimalarial Activity of Artemisinin (Qinghaosu) and Related Trioxanes: Mechanism(s) of Action. In: August, Anders, Murad, and Coyle, eds. *Advances in Pharmacology*. vol. 37. USA: Academic Press, Inc., 253-297.
Vennerstrom et al., "Identification of an antimalarial synthetic trioxolane drug development candidate", *Nature*, 430(7002):900-904 (2004).

*Primary Examiner* — Andrew D Kosar
*Assistant Examiner* — Raymond Covington

(57) ABSTRACT

This invention relates to an improved process for the preparation of a compound of Formula (I), salts of the free base cis-adamantane-2-spiro-3'-8'-[[[(2'-amino-2'-methyl propyl)amino]carbonyl]methyl]-1',2',4'-trioxaspiro[4.5]decane wherein X can be an anion.

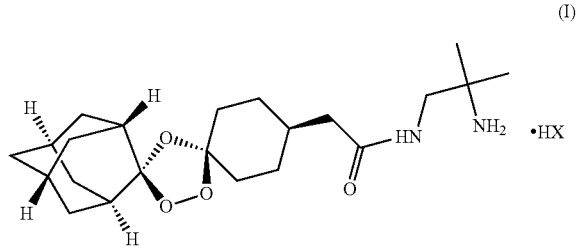

(I)

17 Claims, No Drawings

PROCESS FOR THE PREPARATION OF DISPIRO 1,2,4-TRIOXOLANE ANTIMALARIALS (OZ277)

FIELD OF THE INVENTION

This invention relates to an improved process for the preparation of compounds of Formula I, salts of the free base cis-adamantane-2-spiro-3'-8'-[[[(2'-amino-2'-methyl propyl)amino]carbonyl]methyl]-1',2',4'-trioxaspiro[4.5]decane, which has antimalarial activity,

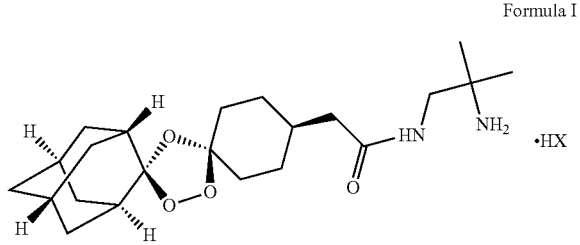

Formula I wherein X is an anion.

BACKGROUND OF THE INVENTION

Malaria is an acute and often chronic infectious disease resulting from the presence of protozoan parasites within red blood cells. Caused by single-celled parasites of the genus *Plasmodium*, malaria is transmitted from person to person by the bite of female mosquitoes.

The discovery of artemisinin (qinghaosu), a naturally occurring endoperoxide sesquiterpene lactone (Meshnick et al., Microbiol. Rev. 60, 301-315, 1996; Vroman et al., Curr. Pharm. Design 5,101-183, 1999; Dhingra et al., Life Sci. 66, 279-300, 2000) initiated a substantial effort to elucidate its molecular mechanism of action (Jefford, Adv. Drugs Res. 29, 271-325, 1997; Cumming et al., Adv. Pharmacol. 37, 254-297, 1997) and to identify novel antimalarial peroxides (Dong and Vennerstrom, Expert Opin. Ther. Patents 11, 1753-1760, 2001). Many synthetic 1,2,4-trioxanes, 1,2,4,5-tetraoxanes, and other endoperoxides have been prepared.

Although the clinically useful semisynthetic artemisinin derivatives are rapid acting and potent antimalarial drugs, they have several disadvantages including recrudescence, neurotoxicity, (Wesche et al., Antimicrob. Agents. Chemother. 38, 1813-1819, 1994) and metabolic instability. (White, Trans. R. Soc. Trop. Med. Hyg. 88, 41-43, 1994). A fair number of these compounds are quite active in vitro, but most suffer from low oral activity. (White, Trans. R. Soc. Trop. Med. Hyg. 88, 41-43, 1994; van Agtmael et al., Trends Pharmacol. Sci. 20, 199-205, 1999). Although many synthetic antimalarial 1,2,4-trioxanes have since been prepared (Jefford, Adv. Drugs Res. 29, 271-325, 1997; Cumming et al., Adv. Pharmacol. 37, 254-297, 1997), there exists a need to identify new antimalarial agents, especially those which are easily synthesized, are devoid of neurotoxicity.

A synthetic procedure for preparing compounds of Formula I, salts of the free base cis-adamantane-2-spiro-3'-8'-[[[(2'-amino-2'-methyl propyl)amino]carbonyl]methyl]-1',2', 4'-trioxaspiro[4.5]decane has been disclosed in U.S. Pat. No. 6,906,205.

SUMMARY OF THE INVENTION

In one aspect, a process for the preparation of compounds of Formula I, resulting in high yields, reduced reaction times and easy isolation of the products is provided. The process is economically attractive, avoids the use of costly chemicals and involves less reaction steps in the reaction sequence.

In another aspect, there is provided an process for the preparation of compounds of Formula I, salts of the free base cis-adamantane-2-spiro-3'-8'-[[[(2'-amino-2'-methyl propyl)amino]carbonyl]methyl]-1',2',4'-trioxaspiro[4.5]decane

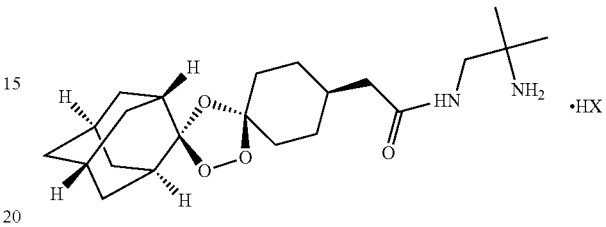

Formula I wherein X is an anion, for example, acetate, adipate, alginate, citrate, aspartate, benzoate, benzene sulfonate, bisulfate, butyrate, camphorate, camphor sulfonate, digluconate, glycerophosphate, glycolate, malonate, hemisulfate, heptanoate, hexanoate, fumarate, hydrochloride, hydrobromide, hydroiodide, isethionate, lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate or undecanoate.

The method comprises the preparation of intermediates of Formula II (wherein R can be alkyl),

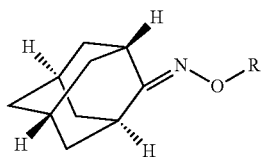

Formula II which in turn comprises reacting a compound of Formula VII

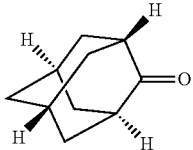

Formula VII with alkoxylamine hydrochloride to give intermediates of Formula II. The process avoids the use of pyridine, which is flammable, difficult to remove and toxic. Also, the work-up in the process of this invention does not involve the use of any solvent. The products are directly isolated by filtration. The short reaction time—about 2 hours—and high yield of about 90% make the process for the preparation of the intermediates is simple, as well as cost effective.

In yet another aspect, a process for the preparation of intermediates of Formula III (wherein R can be alkyl),

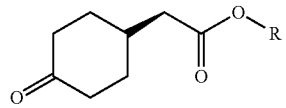

Formula III comprising the oxidation of a compound of Formula VIII in one step,

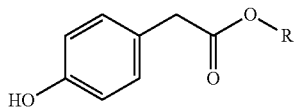

Formula VIII to give intermediates of Formula III. The process can be carried out at about 110 to about 115 psi of hydrogen pressure.

DETAILED DESCRIPTION OF THE INVENTION

The process for the preparation of compounds of Formula I wherein a compound of Formula II (wherein R is lower alkyl) is reacted with a compound of Formula III (wherein R is lower alkyl) to obtain compound of Formula IV;

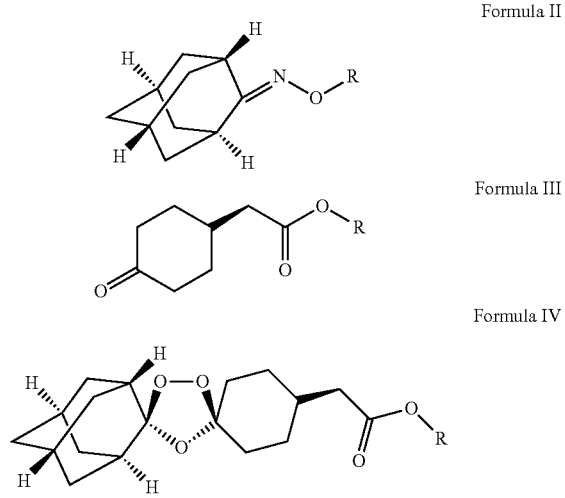

Formula II

Formula III

Formula IV followed by hydrolysis of the compounds of Formula IV to give a compound of Formula V;

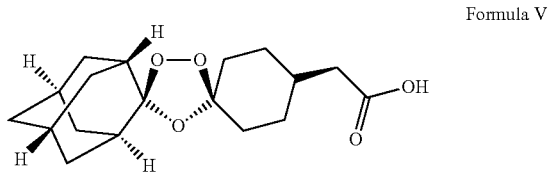

Formula V followed by the reaction of the compound of Formula V with an activating agent, for example, methyl chloroformate, ethyl chloroformate, propyl chloroformate, n-butyl chloroformate, isobutyl chloroformate or pivaloyl chloride leads to the formation of mixed anhydride, which is reacted in situ reaction with 1,2-diamino-2-methyl propane to give a compound of Formula VI; and

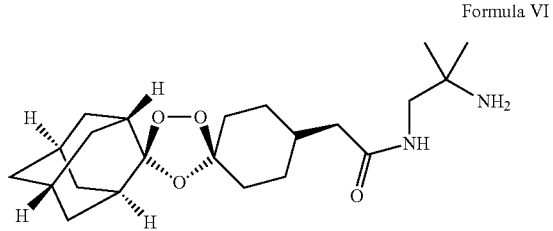

Formula VI reacting the compound of Formula VI with an acid of Formula HX (wherein X can be the same as defined earlier) to give compounds of Formula I.

The reaction of a compound of Formula VII with alkoxylamine hydrochloride to give intermediates of Formula II can be carried out in a solvent, for example, an alcoholic solvent, for example, methanol, ethanol or isopropanol, water or mixture(s) thereof.

The reaction of a compound of Formula VII with alkoxylamine hydrochloride can be carried out in the presence of an inorganic base, for example, sodium hydroxide, potassium hydroxide or mixture(s) thereof.

The oxidation of a compound of Formula VIII to give intermediates of Formula III can be carried out in a hydrocarbon solvent, for example, O-xylene, toluene, benzene or mixture(s) thereof. The oxidation step can be carried out in the presence of a catalyst, for example, palladium on carbon at a temperature of 80-200° C.

The reaction of a compound of Formula II with a compound of Formula III to give a compound of Formula IV can be carried out in a hydrocarbon solvent, for example, hexane or cyclohexane, chlorinated hydrocarbon solvent, for example, dichloromethane or dichloroethane or mixture(s) thereof.

The hydrolysis of compounds of Formula IV to give a compound of Formula V can be carried out in a solvent, for example, an alcoholic solvent, for example, methanol, ethanol or isopropanol, water or mixture(s) thereof.

The hydrolysis of a compound of Formula IV can be carried out in the presence of an inorganic base, for example, sodium hydroxide, potassium hydroxide or mixture(s) thereof.

The reaction of a compound of Formula V with an activating agent and 1,2-diamino-2-methyl propane to give a compound of Formula VI can be carried out in a chlorinated hydrocarbon solvent, for example, dichloromethane or dichloroethane, polar aprotic solvent, for example, dimethylformamide or dimethylsulfoxide or mixture(s) thereof.

The reaction of a compound of Formula V with an activating agent and 1,2-diamino-2-methyl propane can be carried out in the presence of an organic base, for example, trimethyl amine, triethyl amine, isopropyl amine or mixture(s) thereof.

The reaction of a compound of Formula VI with an acid of Formula HX to give a compound of Formula I can be carried out in a solvent, for example, an alcoholic solvent, for example, methanol, ethanol or isopropanol, hydrocarbon solvent, for example, hexane or heptane or mixture(s) thereof.

While the present invention has been described in terms of its specific embodiments, certain modifications and equivalents will be apparent to those skilled in the art and are included within the scope of the present invention. The examples are provided to illustrate particular aspects of the disclosure and do not limit the scope of the invention.

EXAMPLES

Example 1

Preparation of O-methyl-2-adamantanone oxime

To a solution of 2-adamantanone (50 g, 0.3328 mol, 1 equiv.) in methanol (0.25 lit), sodium hydroxide solution (15 g, 0.3761 mol, 1.13 equiv, in 50 mL water) was added followed by methoxylamine hydrochloride (37.5 g×81.59% Purity=30.596 g, 0.366 mol, 1.1 equiv) at room temperature under stirring. The reaction mixture was stirred at room temperature for 1 to 2 h. The reaction was monitored by HPLC. The reaction mixture was concentrated at 40-45° C. under vacuum to get a thick residue. Water (250 mL) was added at room temperature and the reaction mixture was stirred for half an hour. The white solid was filtered, washed with water (50 mL), and dried at 40 to 45° C. under reduced pressure. O-methyl 2-adamantanone oxime (57 g, 95% yield) was obtained as a white solid.

($M^+$+1) 180, $^1$HNMR (400 MHz, CDCl$_3$): δ 1.98-1.79 (m, 12H), 2.53 (s, 1H), 3.46 (s, 1H), 3.81 (s, 3H).

Example 2

Preparation of 4-(methoxycarbonymethyl)cyclohexanone

A high pressure autoclave was charged with a mixture of methyl (4-hydroxyphenyl)acetate (50 g, 0.30 mol), palladium (5 g) (10%) on carbon (50% wet) and O-xylene (250 mL). The reaction mixture was stirred under 110 to 115 psi of hydrogen pressure for 7 to 8 h at 140° C. The reaction was monitored by HPLC. The reaction mixture was then cooled to room temperature, and the catalyst was filtered off. Filtrate was concentrated under reduced pressure to get 4-(methoxycarbonylmethyl)cyclohexanone as light yellow to colorless oily liquid (48.7 g, 97.4%).

($M^+$+1) 171, $^1$HNMR (400 MHz, CDCl$_3$): δ 1.48-1.51 (m, 2H), 2.11-2.07 (m, 2H), 2.4-2.23 (m, 7H), 3.7 (s, 3H).

Example 3

Preparation of methyl (1 s, 4 s)-dispiro[cyclohexane-1,3'-[1,2,4]trioxolane-5', 2''-tricyclo[3.3.1.1$^{3,7}$]decan]-4-ylacetate A solution of O-methyl-2-adamantanone oxime (example 1) (11.06 g, 61.7 mmol, 1.5 equiv.) and 4-(methoxycarbonymethyl)cyclohexanone (example 2) (7.0 g, 41.1 mmol, 1 equiv.) in cyclohexane (200 ml) and dichloromethane (40 mL) was treated with ozone (ozone was produced with an OREC ozone generator [0.6 L/min. O$_2$, 60 V] passed through an empty gas washing bottle that was cooled to −78° C.). The solvent was removed after the reaction was complete. After removal of solvents, the crude product was purified by crystallization from 80% aqueous ethanol (200 mL) to afford the title compound as a colorless solid. Yield: 10.83 g, 78%, mp: 96-98° C.; $^1$HNMR (500 Hz, CDCl$_3$): δ 1.20-1.33 (m, 2H), 1.61-2.09 (m, 21H), 2.22 (d, J=6.8 Hz, 2H), 3.67 (s, 3H).

Example 4

Preparation of (1 s, 4 s)-dispiro[cyclohexane-1,3'-[1,2,4]trioxolane-5',2''-tricyclo[3.3.1.1$^{3,7}$]decan]-4 ylacetic acid Sodium hydroxide (3.86 g, 96.57 mmol, 3 equiv.) in water (80 mL) was added to a solution of methyl (1 s, 4 s)-dispiro[cyclohexane-1,3'-[1,2,4]trioxolane-5',2''-tricyclo[3.3.1.1$^{3,7}$]decan]-4-ylacetate (example 3) (10.83 g, 32.19 mmol, 1 equiv.) in 95% ethanol (150 mL). The mixture was stirred at 50° C. for about 4 h, cooled to 0° C., and treated with 1M hydrochloric acid (129 ml, 4 equiv). The precipitate was collected by filtration, washed with 50% aqueous ethanol (150 mL) and dried in vacuum at 40° C. to give the title compound as colorless solid. Yield: 9.952 g, 96%, mp: 146-148° C. (95% ethanol), $^1$HNMR (500 Hz, CDCl$_3$): δ 1.19-1.41 (m, 2H), 1.60-2.05 (m, 21H), 2.27 (d, J=6.8 Hz, 2H).

Example 5

Preparation of cis-adamantane-2-spiro-3'-8'-[[[(2'-amino-2'-methyl propyl)amino]carbonyl]methyl]-1',2',4'-trioxaspiro[4.5]decane Method A:

(1 s, 4 s)-dispiro[cyclohexane-1,3'-[1,2,4]trioxolane-5',2''-tricyclo[3.3.1.1$^{3,7}$]decan]-4-ylacetic acid (example 4) (5 g, 15.5 mmol, 1 equiv) was mixed with triethylamine (2.5 g, 24.8 mmol, 1.6 equiv) in 100 ml of dichloromethane. The reaction mixture was cooled to −10° C. to 0° C. Ethyl chloroformate (1.68 g, 17 mmol, 1.0 equiv) in 15 mL dichloromethane was charged to the above reaction mixture at −10° C. to 0° C. The reaction mixture was stirred at the same temperature for 10 to 30 minutes. The resulting mixed anhydride reaction mixture was added dropwise to a previously prepared solution of 1,2-diamino-2-methylpropane (1.64 g, 18.6 mmol, 1.2 equiv), in 100 mL dichloromethane at −10° C. to 0° C. The temperature of reaction mixture was raised to room temperature. The reaction mixture was stirred at the same temperature till the reaction was complete. Reaction monitoring was done by thin layer chromatography using 5 to 10% methanol in dichloromethane. The reaction was complete within 2 h. Nitrogen atmosphere was maintained throughout the reaction. Water (50 mL) was charged, organic layer was separated and washed with 10% sodium bicarbonate solution (50 mL) and water (50 mL) at room temperature. The organic layer was dried over sodium sulphate and the solvent was removed at 25 to 40° C. under reduced pressure. Hexane (50 ml) was added to obtain residue under stirring at room temperature. The mixture was filtered and washed with 5 mL of chilled hexane. The solid was dried under reduced pressure at room temperature.

Yield: 5.2 g (85.4%), ($M^+$+1) 393, $^1$HNMR (400 MHz, DMSO-d$_6$): δ 0.929 (s, 6H), 1.105-1.079 (m, 2H), 1.887-1.641 (m, 21H), 2.030-2.017 (d, 2H), 2.928 (d, 2H).

Method B:

(1 s, 4 s)-dispiro[cyclohexane-1,3'-[1,2,4]trioxolane-5',2''-tricyclo[3.3.1.1$^{3,7}$]decan]-4-ylacetic acid (example 4) (10 g, 31 mmol, 1 equiv) was treated with isobutyl chloroformate (4.5 g, 33 mmol, 1.1 equiv) in presence of organic base like triethyl amine (5 g, 49.6 mmol, 1.6 equiv) at 0° C. to 7° C. in 250 ml of dichloromethane. The solution was stirred at 0° C. to 7° C. for about 10 to 30 minutes. To the above reaction mixture, previously prepared solution of 1,2-diamino-2-methylpropane (3.27 g, 37 mmol, 1.2 equiv), in 50 mL of dichloromethane was added at 0° C. to 7° C. in one lot. The temperature of reaction mixture was raised to room temperature. The reaction mixture was stirred at the room temperature till reaction was over. Reaction monitoring was done by thin layer chromatography using 5 to 10% methanol in dichloromethane. Reaction was complete within 2 h. The reaction nitrogen atmosphere was maintained throughout the reaction. Water (250 mL) was charged, organic layer was separated and washed with 10% sodium bicarbonate solution (200 mL) and water (100 mL) at room temperature and the solvent was removed at 25 to 40° C. under reduced pressure. Hexane (100 ml) was added to the residue, under stirring, at room temperature. The mixture was filtered and washed with chilled hexane (10 mL). The resultant solid was dried under reduced pressure at room temperature. Yield: 10.63 g (87%), (M$^+$+1) 393, $^1$HNMR 15 (400 MHz, DMSO-d$_6$): δ 0.928 (s, 6H), 1.102-1.074 (m, 2H), 1.859-1.616 (m, 21H), 2.031-2.013 (d, 2H), 2.94-2.925 (d, 2H).

Method C:

(1 s, 4 s)-dispiro[cyclohexane-1,3'-[1,2,4]trioxolane-5',2''-tricyclo[3.3.1.1$^{3,7}$]decan]-4-ylacetic acid (example 4) (5 g, 15.5 mmol, 1 equiv) was treated with pivaloyl chloride (1.87 g, 15.5 mmol, 1 equiv) and triethylamine (2.5 gm, 24.8 mmol, 1.6 equiv) at −15° C. to −10° C. in dichloromethane (125 mL). The solution was stirred at −15° C. to −10° C. for about 10 to 30 minutes. It resulted in the formation of mixed anydride. To the above reaction mixture, previously prepared solution of 1,2-diamino-2-methylpropane (1.64 g, 18.6 mmol, 1.2 equiv) in 25 mL dichloromethane was added at −15° C. to −10° C. The temperature of reaction mixture was raised to room temperature. The reaction mixture was stirred at the room temperature till reaction was over. Reaction monitoring was done by thin layer chromatography using 5 to 10% methanol in dichloromethane. The reaction was complete within 2 h. Nitrogen atmosphere was maintained throughout the reaction. Water (125 mL) was charged, organic layer was separated and washed with 50 mL of 10% sodium bicarbonate solution and 125 mL of water, respectively at room temperature. Finally solvent was removed at 25 to 40° C. under reduced pressure. 50 mL of 5% Ethyl acetate-hexane solvent mixture was added to the residue under stirring at room temperature. The mixture was filtered and washed with 5 mL of chilled hexane. Solid was dried under reduced pressure at room temperature. Yield: 5.03 g (83%), (M$^+$+1) 393, $^1$HNMR (400 MHz, DMSO-d$_6$): δ 0.93 (s, 6H), 1.113-1.069 (m, 2H), 1.861-1.644 (m, 21H), 2.033-2.015 (d, 2H), 2.948-2.933 (d, 2H).

Example 6

Preparation of cis-adamantane-2-Spiro-3'-8'-[[[(2'-amino-2'-methyl propyl)amino]carbonyl]methyl]-1',2',4'-trioxaspiro[4.5]decane maleate To a solution of cis-adamantane-2-spiro-3'-8'-[[[(2'-amino-2'-methyl propyl)amino]carbonyl]methyl]-1',2',4'-trioxaspiro[4.5]decane (example 5) (60 g, 0.153 moles) in ethanol (150 mL) was added a solution of maleic acid (17.3 g, 0.15 moles, 0.98 equiv. in ethanol 90 mL) and the reaction mixture was stirred for about 1 h. To this clear solution, n-heptane (720 mL) was added at room temperature in 1 h and the reaction mixture was stirred for 3 h. It was then cooled to 0 to 10° C. and filtered. The cake was washed with n-heptane (60 mL) and dried under vacuum at 40-45° C.

Yield: 67 g, 77.4%, mp: 149° C. (decomp), (M$^+$+1) 393.5, $^1$HNMR (300 MHz, DMSO-d$_6$): δ 1.05-1.11 (2H, m), 1.18 (6H, s), 1.64-1.89 (21H, m), 2.07 (2H, d), 3.21 (2H, d), 6.06 (2H, d), 7.797 (2H, bs), 8.07 (1H, t).

We claim:

1. A process for the preparation of a compound of Formula I, salt of the free base cis-adamantane-2-spiro-3'-8'-[[[(2'-amino-2'-methyl propyl)amino]carbonyl]methyl]-1',2',4'-trioxaspiro [4.5] decane

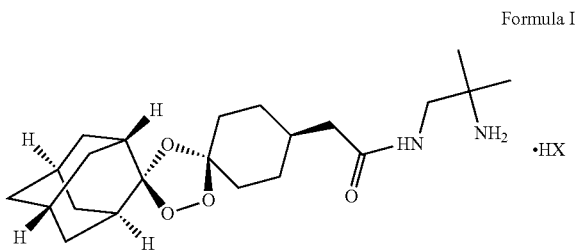

Formula I wherein X is an anion selected from acetate, adipate, alginate, citrate, aspartate, benzoate, benzene sulfonate, bisulfate, butyrate, camphorate, camphor sulfonate, digluconate, glycerophosphate, glycolate, malonate, hemisulfate, heptanoate, hexanoate, fumarate, hydrochloride, hydrobromide, hydroiodide, isethionate, lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate or undecanoate, the process comprising, a) reacting a compound of Formula II (wherein R is alkyl) with a compound of Formula III (wherein R is alkyl)

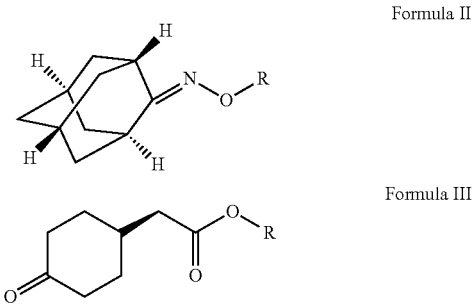

Formula II

Formula III to give a compound of Formula IV;

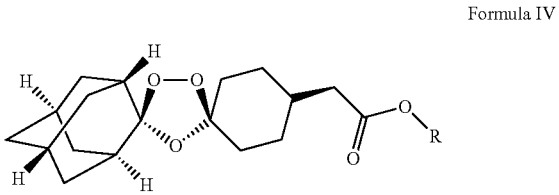

Formula IV b) hydrolyzing the compound of Formula IV to give a compound of Formula V;

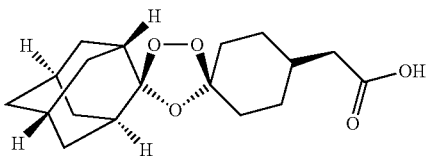

Formula V c) reacting the compound of Formula V with an activating agent that forms a mixed anhydride with the compound of Formula V and 1,2-diamino-2-methyl propane to give a compound of Formula VI; and

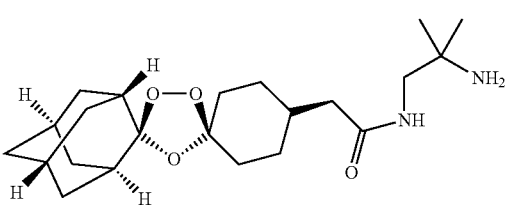

Formula VI d) reacting the compound of Formula VI with an acid of Formula HX (wherein X is the same as defined earlier) to give a compound of Formula I.

2. The process according to claim 1, wherein the activating agent is selected from methyl chloroformate, ethyl chloroformate, propyl chloroformate, n-butyl chloroformate, isobutyl chloroformate and pivaloyl chloride.

3. The process according to claim 1, wherein the reaction of a compound of Formula II with a compound of Formula III to give a compound of Formula IV is carried out in a hydrocarbon solvent, chlorinated hydrocarbon solvent or mixture(s) thereof.

4. The process according to claim 3, wherein the hydrocarbon solvent is hexane, cyclohexane or mixture(s) thereof.

5. The process according to claim 3, wherein the chlorinated hydrocarbon solvent is dichloromethane, dichloroethane or mixture(s) thereof.

6. The process according to claim 1, wherein the hydrolysis of a compound of Formula IV to give a compound of Formula V is carried out in an alcoholic solvent, water or mixture(s) thereof.

7. The process according to claim 6, wherein the alcoholic solvent is methanol, ethanol, isopropanol or mixture(s) thereof.

8. The process according to claim 1, wherein the hydrolysis of a compound of Formula IV to give a compound of Formula V is carried out in the presence of an inorganic base.

9. The process according to claim 8, wherein the inorganic base is sodium hydroxide, potassium hydroxide or mixture(s) thereof.

10. The process according to claim 1, wherein the reaction of a compound of Formula V with an activating agent and 1,2-diamino-2-methyl propane to give a compound of Formula VI is carried out in a chlorinated hydrocarbon solvent, polar aprotic solvent or mixture(s) thereof.

11. The process according to claim 10, wherein the chlorinated hydrocarbon solvent is dichloromethane, dichloroethane or mixture(s) thereof.

12. The process according to claim 10, wherein the polar aprotic solvent is dimethylformamide, dimethylsulfoxide or mixture(s) thereof.

13. The process according to claim 10, wherein the reaction of a compound of Formula V with an activating agent and 1,2-diamino-2-methyl propane to give a compound of Formula VI is carried out in the presence of an organic base.

14. The process according to claim 13, wherein the organic base is trimethylamine, triethylamine, isopropylamine or mixture(s) thereof.

15. The process according to claim 1, wherein the reaction of a compound of Formula VI with an acid of Formula HX to give a compound of Formula I is carried out in an alcoholic solvent, hydrocarbon solvent or mixture(s) thereof.

16. The process according to claim 15, wherein the alcoholic solvent is methanol, ethanol, isopropanol or mixture(s) thereof.

17. The process according to claim 15, wherein the hydrocarbon solvent is hexane, heptane or mixture(s) thereof.

* * * * *

UNITED STATES PATENT AND TRADEMARK OFFICE
CERTIFICATE OF CORRECTION

PATENT NO. : 8,569,519 B2  
APPLICATION NO. : 12/301823  
DATED : October 29, 2013  
INVENTOR(S) : Gyan Chand Yadav et al.

Page 1 of 1

It is certified that error appears in the above-identified patent and that said Letters Patent is hereby corrected as shown below:

In the Specification

Column 5, lines 53: "Preparation of methyl (1 s, 4 s)-dispiro[cyclohexane-" should read  
-- Preparation of methyl (1s, 4s)-dispiro[cyclohexane- --

Column 6, lines 6-8: "Preparation of (1 s, 4 s)-dispiro[cyclohexane-1,3'-[1,2,4]trioxolane-5',2"-tricyclo[3.3.1.1 ] decan]-4ylacetic acid" should read  
-- Preparation of (1s, 4s)-dispiro[cyclohexane-1,3'-[1,2,4]trioxolane-5',2"-tricyclo[3.3.1.1 ]decan]-4-ylacetic acid --

Column 6, line 11: "(80 mL) was added to a solution of methyl (1 s, 4 s)-dispiro" should read  
-- (80 mL) was added to a solution of methyl (1s, 4s)-dispiro --

Column 6, line 30: "(1 s, 4 s)-dispiro[cyclohexane-1,3'-[1,2,4]trioxolane" should read  
-- (1s, 4s)-dispiro[cyclohexane-1,3'-[1,2,4]trioxolane --

Column 6, line 61: "(1 s, 4 s)-dispiro[cyclohexane-1,3'-[1,2,4]trioxolane-5',2"-" should read  
-- (1s, 4s)-dispiro[cyclohexane-1,3'-[1,2,4]trioxolane-5',2"- --

Column 7, line 19: Delete the number "15" immediately following "HNMR"

Column 7, line 23: "(1 s, 4 s)-dispiro[cyclohexane-1,3'-[1,2,4]trioxolane-5',2"-" should read  
-- (1s, 4s)-dispiro[cyclohexane-1,3'-[1,2,4]trioxolane-5',2"- --

Signed and Sealed this  
Twenty-seventh Day of January, 2015

Michelle K. Lee  
*Deputy Director of the United States Patent and Trademark Office*